United States Patent [19]

Werner

[11] 3,933,906
[45] Jan. 20, 1976

[54] 3,4-BISAMINO-5-SULFAMOYLBENZOIC ACIDS

[75] Inventor: Lincoln Harvey Werner, Summit, N.J.

[73] Assignee: Ciba-Geigy Corporation, Ardsley, N.Y.

[22] Filed: Aug. 8, 1973

[21] Appl. No.: 386,651

Related U.S. Application Data

[63] Continuation-in-part of Ser. No. 297,531, Oct. 13, 1972.

[52] U.S. Cl. ... 260/518 R; 260/247.1; 260/268 PH; 260/293.73; 260/326.13 R; 260/345.7; 260/347.2; 260/465 D; 260/470; 260/501.11; 260/518 A; 260/519; 424/248; 424/267; 424/274; 424/285; 424/304; 424/310; 424/319
[51] Int. Cl.² .................................. C07C 143/52
[58] Field of Search ............ 260/518 R, 518 A, 519

[56] References Cited
UNITED STATES PATENTS 3,706,790  12/1972  Sprague et al. ............... 260/518 R
3,780,027  12/1973  Cragoe et al. ................. 260/518 R
3,790,584  2/1974   Feit et al. ..................... 260/518 R Primary Examiner—Anton H. Sutto
Assistant Examiner—L. A. Thaxton
Attorney, Agent, or Firm—Joseph G. Kolodny; Theodore O. Groeger; John J. Maitner

[57] ABSTRACT

3-Amino-4-anilino-5-sulfamoylbenzoic acids, e.g. those of the formula

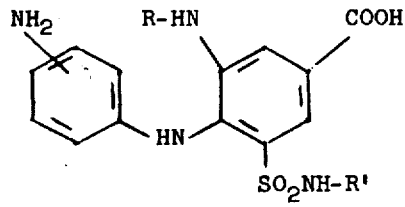

R = an aliphatic or araliphatic radical
R' = H, alkyl, or aminophenyl
alkyl esters or salts thereof are diuretic agents.

4 Claims, No Drawings

3,4-BISAMINO-5-SULFAMOYLBENZOIC ACIDS

CROSS-REFERENCE TO RELATED APPLICATION

This is a continuation-in-part of application Ser. No. 297,531, filed Oct. 13, 1972.

BACKGROUND OF THE INVENTION

Pursuant to the discovery of the diuretic 4-halo-5-sulfamoyl-anthranilic acids, substituted at the sulfamoyl moiety by an araliphatic or aromatic radical, described in my U.S. Pat. Nos. 3,565,920 or 3,658,990, there was generated a new class of primary amino compounds herein described, which members surprisingly do not require a halogen atom or a tertiary amino group at the aromatic nucleus, thought to be essential for diuretics, such as the chlorothiazides, hydrochlorothiazides or said anthranilic acids, or the sulfamoylbenzoic acids described in U.S. Pat. Nos. 2,937,169 and 3,163,645 or Belgian Pat. No. 743,744 respectively.

SUMMARY OF THE INVENTION

The present invention concerns and has for its object the provision of new 3-amino-4-anilino-5-sulfamoyl-benzoic acids, the lower alkyl esters and therapeutically acceptable salts thereof, more particularly of those corresponding to Formula I

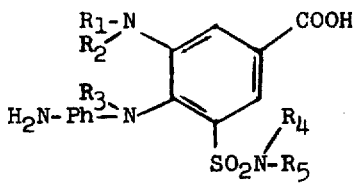

(I)

in which $R_1$ is an aliphatic or araliphatic radical, $R_2$ is hydrogen or an aliphatic radical, each of $R_3$ and $R_4$ is hydrogen or lower alkyl, Ph is a phenylene radical and $R_5$ is hydrogen, lower alkyl or Ph—$NH_2$, or the lower alkyl esters or therapeutically useful ammonium, alkali or alkaline earth metal or acid addition salts thereof, as well as of corresponding pharmaceutical compositions and of methods for the preparation and application of these products, which are useful, orally applicable diuretic, natri- and chloriuretic agents.

DESCRIPTION OF THE PREFERRED EMBODIMENTS

An aliphatic radical $R_1$ or $R_2$ is, for example, lower alkyl, e.g. methyl, ethyl, n- or i-propyl, n-, i- or sec. butyl, n- or i-pentyl, neopentyl, n-hexyl or n-heptyl; lower alkenyl, e.g. allyl, methallyl or 2-butenyl; lower alkynyl, e.g. propargyl; mono- or bicyclic cycloalkyl, cycloalkenyl, cycloalkyl-lower alkyl or cycloalkenyl-lower alkyl with preferably 3 to 7 ring-carbon atoms, 1 to 4 chain carbon atoms and optional, e.g. up to 4, lower alkyl groups, e.g. cyclopropyl, 2,3-dimethylcyclopropyl, cyclobutyl, cyclopentyl, 2- or 3-methyl-cyclopentyl, 2,5- or 3,4-dimethylcyclopentyl, cyclohexyl, 2-, 3- or 4-methyl-cyclohexyl, 2,3-, 2,4- or 3,5-dimethyl-cyclohexyl, 2,4,6-trimethyl-cyclohexyl, cycloheptyl, cyclooctyl, 2- or 7-norbornanyl, 1- or 2-decahydronaphthyl; 1- or 2-cyclopentenyl, 2,4-cyclopentadienyl, 2- or 3-methyl-2-cyclopentenyl, 4,5-dimethyl-2-cyclopentenyl, 1-, 2- or 3-cyclohexenyl, 2,5-cyclohexadienyl, 2-, 3- or 4-methyl-1- or 2-cyclohexenyl, 2,4- or 3,5-dimethyl-1- or 2-cyclohexenyl, 2,4,6-trimethyl-2,5-cyclohexadienyl, 1-, 2- or 3-cycloheptenyl, 2,6-cycloheptadienyl, 2-cyclooctenyl or 2-norborn-5-enyl, as well as the corresponding cycloalkyl- or cycloalkenyl-lower alkyl groups in which the chain especially represents methyl, but also ethyl n- or i-propyl, n-, i- or sec. butyl; it contains in any of the positions available for substitution one of the specific cycloalkyl or cycloalkenyl groups listed above. The term "lower", referred to above and hereinafter in connection with organic radicals or compounds respectively, defines such with up to 7, preferably up to 4, carbon atoms.

Said aliphatic radicals, especially the lower alkyl groups, can be substituted, e.g. by free or functionally converted hydroxy, mercapto or carboxy groups and/or interrupted by heteratoms, e.g. one oxygen, sulfur and/or nitrogen atom, and are represented, for example, by lower haloalkyl, e.g. 2-(chloro, bromo or iodo)-ethyl, 3,3-difluoro- or dichloropropyl, 3,3,3-trichloropropyl, 3- or 4-chlorobutyl, 4,4- or 3,4-dichlorobutyl or 4,4,4-trifluorobutyl; unsubstituted or halogenated lower alkoxy- or alkylmercapto-lower alkyl, such as 2-ethoxyethyl, 3-methoxy-propyl, 2-ethylmercapto-ethyl, 2-(2,2-dichloroethoxy)-ethyl, 2-(2-chloroethoxy)-ethyl, 2-(2,2,2-trifluoroethylmercapto)-ethyl or 2-(2,2-dichloroethylmercapto)-ethyl; carbamyl-lower alkyl or N,N-di-lower alkylcarbamyl-lower alkyl, such as carbamyl-methyl, N,N-dimethylcarbamyl-methyl, 2-carbamyl-ethyl or 2-N,N-diethylcarbamyl-ethyl; sec. or tert. amino-lower alkyl, such as mono- or di-lower alkylamino-lower alkyl, lower alkyleneimino-lower alkyl, lower monoaza-, -oxa- or -thiaalkyleneimino-lower alkyl or N-lower alkyl-lower monoazaalkyleneimino-lower alkyl, e.g. 2-ethylaminoethyl, 2-dimethylaminoethyl, 3-diethylamino-propyl, 2-pyrrolidinoethyl, 2-piperidino-ethyl, 2-(4-methyl-piperazino)-ethyl or 2-morpholino-ethyl; 5 to 7 ring-membered oxa-cycloalkyl or -cycloalkenyl, oxa-cycloalkyl- or -cycloalkenyl-lower alkyl, such as 3-tetrahydrofuryl, tetrahydrofuryl-2-methyl, (2-methyl-tetrahydrofuryl-2)-methyl, 2,3-dihydro- or tetrahydropyranyl-2-methyl.

An araliphatic radical $R_1$ preferably represents H-Ph-lower alkyl or -alkenyl or Hc-lower alkyl or -alkenyl, in which the alkyl or alkenyl moiety preferably has up to 4 chain carbon atoms. Ph is a phenylene radical, which is either unsubstituted or substituted by one or more than one, preferably one or two substituents selected, for example, from lower alkyl, e.g. that mentioned above, free or functionally converted hydroxy or mercapto, such as lower alkoxy, lower alkylenedioxy, lower alkylmercapto or halogeno, e.g. methoxy, ethoxy, n- or i-propoxy or -butoxy; methylenedioxy, 1,1- or 1,2-ethylenedioxy; methyl- or ethylmercapto; fluoro, chloro or bromo; (hydroxy or halogeno)-lower alkyl or -alkoxy, e.g. 2-hydroxyethyl, trifluoromethyl or 2-hydroxyethoxy; nitro; amino, especially di-lower alkylamino, e.g. dimethylamino or diethylamino; or free or functionally converted carboxy or sulfo, e.g. lower carbalkoxy, carbamoyl, cyano or sulfamoyl. Hc is either unsubstituted pyridyl, furyl, or thienyl, or such radical substituted by one or more than one, preferably one or two lower alkyl groups.

Preferred araliphatic or aromatic radicals $R_1$, $R_5$ and $H_2N-Ph$ are represented by the formulae $H-Ph'-C_mH_{2m}$, $Hc'-C_mH_{2m}$ and $H_2N-Ph'-C_mH_{2m}$ respectively, wherein $Ph'$ is unsubstituted 1,2-phenylene, advantageously 1,3-phenylene or preferably 1,4-phenylene, or such radicals substituted by one member of the group consisting of lower alkyl, hydroxy, lower alkoxy, halogeno or trifluoromethyl; $Hc'$ is unsubstituted 2-, 3-, or 4-pyridyl, 2- or 3-furyl or -thienyl, or such radicals substituted by one or two lower alkyl groups and $m$ is an integer from 0 to 4.

Each of $R_2$, $R_3$, $R_4$ and $R_5$ is preferably hydrogen, but also lower alkyl, e.g. that mentioned above, advantageously methyl. $R_2$, moreover, represents lower alkenyl or alkynyl, also mentioned above, especially 2-butenyl, and $R_5$ may also represent $Ph'-NH_2$.

Preferred esters of the acids of Formula I are the methyl, ethyl, n- or i-propyl or -butyl esters and of the salts the ammonium, sodium, potassium, magnesium or calcium salts are preferred. Due to the amino groups present, also acid addition salts can be prepared, e.g. such of the therapeutically useful acids listed below.

The compounds of the invention exhibit valuable pharmacological properties. Primarily they show diuretic, natri- and chloriuretic activity with rapid onset of action, high urine but low potassium excretion levels. This can be demonstrated in animal tests using, for example mammals, e.g. rats or dogs, as test objects. Such tests are performed, for example, by administering the compounds of the invention within a gelatin capsule to dogs, or in the form of aqueous solutions or starch suspensions by stomach tube to rats, in an oral dosage range between about 0.01 and 50 mg/kg/day, preferably between about 0.1 and 10 mg/kg/day, advantageously between about 0.5 and 5 mg/kg/day. Simultaneously the test animals may receive various salt loads enterally or parenterally, for example, various amounts of subcutaneously applied 0.9% saline, e.g. 100 ml thereof per medium-sized dog (beagle). Urine is then collected, e.g. at 2 hour intervals, with or without catheterization, and its volume, sodium, potassium and chloride content estimated and compared with that of the same untreated or saline-treated animals. Besides the anti-edematous utility, the compounds of the invention can also be used as intermediates in the preparation of other valuable products, primarily, of pharmacologically active compounds or compositions, e.g. such useful in the management of hypertension.

Preferred and highly diuretic are those compounds of Formula I in which $R_1$ is lower alkyl, lower alkenyl, lower alkynyl, (monocyclic, 3 to 7 ring-membered cycloalkyl, cycloalkenyl, oxacycloalkyl, 2- or 7-norbornanyl or 2-norborn-5-enyl)-$C_mH_{2m}$, $H-Ph'-C_nH_{2n}$, $H-Ph'-CH=CH-CH_2$ or $Hc'-C_nH_{2n}$ wherein $Ph'$ is 1,2-, 1,3- or 1,4-phenylene, unsubstituted or substituted by one member of lower alkyl, hydroxy, lower alkoxy, halogeno or trifluoromethyl, $Hc'$ is 2-, 3- or 4-pyridyl, 2- or 3-furyl or -thienyl, unsubstituted or substituted by one or two lower alkyl groups, m is an integer from 0 to 4 and $n$ is an integer from 1 to 4, $R_2$ is hydrogen, lower alkyl, lower alkenyl or lower alkynyl, each of $R_3$ and $R_4$ is hydrogen or lower alkyl, Ph is the above $Ph'$, and $R_5$ is hydrogen, lower alkyl or $Ph'-NH_2$, or the lower alkyl esters or therapeutically useful ammonium, alkali or alkaline earth metal or acid addition salts thereof.

Especially valuable and suitable for said utility are the compounds of Formula II

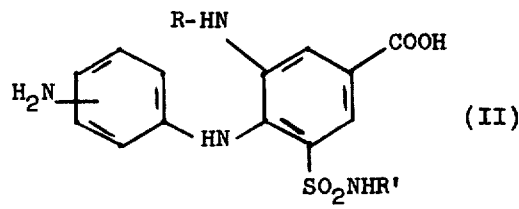

(II)

wherein R is alkyl or alkenyl with 3 to 7 carbon atoms, (3 to 7 ring-membered cycloalkyl, tetrahydrofuryl, 2- or 7-norbornanyl, 2-norborn-5-enyl, phenyl, tolyl, anisyl, halophenyl, furyl or thienyl)-methyl or -ethyl, or cinnamyl, R' is hydrogen or aminophenyl, or therapeutically useful ammonium alkali metal, or acid addition salts thereof.

Outstandingly active compounds are those of Formula II, wherein R is alkyl or 2-alkenyl with 4 or 5 carbon atoms, cyclopropylmethyl, 2-tetrahydrofurylmethyl, 2-norborn-5-enylmethyl, benzyl, furfuryl or cinnamyl and R' is hydrogen, or therapeutically useful ammonium, alkali metal or acid addition salts thereof.

Most preferred are the 4-(4-aminophenylamino)-3-(n-butyl, benzyl or furfuryl)-amino-5-sulfamoylbenzoic acids which, when given to rats or dogs at oral doses as low as 0.3 mg/kg/day, exhibit outstanding diuretic, natri- and chloriuretic effects.

The compounds of the invention are prepared according to methods in themselves known. Advantageously they are obtained by:

a. converting in a compound of Formula III

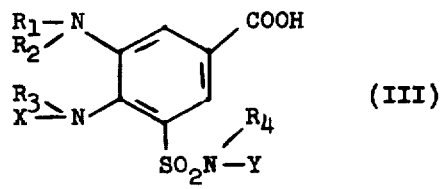

(III)

wherein X is an (acylamino, nitro or arylazo)-Ph radical, and Y is $R_5$ or X, or a lower alkyl ester or salt thereof, X and Y into the corresponding aminophenyl group by hydrolysis or hydrogenation respectively or b. converting in a compound of Formula IV

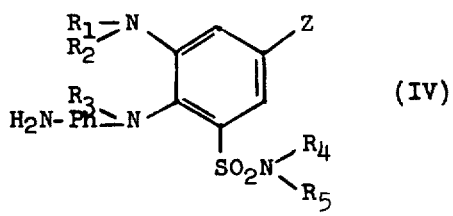

(IV)

wherein Z is a carbamoyl or aminocarbamoyl group, or a salt thereof, Z into carboxy, carbalkoxy or salified carboxy by hydrolysis or alcoholysis and, if desired, converting any resulting compound into another compound of the invention.

In said compounds of Formula III containing the (acylamino, nitro or arylazo)-Ph radical X and, as the case may be, Y also, the acylamino group is advantageously derived from either a lower alkanoic or a carbonic acid lower alkyl ester and the arylazo group is preferably that of the formula H—Ph—N=N—. Said acylaminophenyl compounds, preferably the (low alkanoyl- or lower alkoxycarbonylamino)-Ph, e.g. the (acetyl-, propionyl- or ethoxycarbonylamino)-Ph compounds, are converted into the compounds of the invention by hydrolysis, for example, with the use of hot aqueous bases, such as aqueous alkali metal hydroxides or carbonates or quaternary ammonium hydroxides, e.g. sodium hydroxide, potassium carbonate or trimethylbenzyl-ammonium hydroxide. In case X and Y stand for said (nitro or arylazo)-Ph group, it is converted into aminophenyl by conventional reduction, for example, with the use of catalytically activated or nascent hydrogen, e.g. hydrogen in the presence of platinum, palladium or nickel catalysts, e.g. Raney nickel, or generated by the action of non-precious metals, e.g. zinc or iron, on acids, such as mineral acids, e.g. hydrochloric or sulfuric acid, or with the use of reducing agents, preferably salts of elements of the 4th to 6th group of the Periodic Table and being in a low oxidation state, such as stannous or chromous halides, ammonium polysulfides or alkali metal hydrosulfites.

The carbamoyl or aminocarbamoyl group Z in said compounds of Formula IV is preferably unsubstituted, but may also be substituted by lower alkyl, aralkyl or aryl radicals, e.g. $R_1$, Ph—$NH_2$ or X. The corresponding amides or hydrazides, e.g. the mono- or dimethylamide, diethylamide, i-propylamide; benzylamide or acetylaminophenylamide, or the corresponding hydrazides, are hydrolyzed or alcoholized to the compounds of Formula I, their lower alkyl esters or salts, according to conventional methods, advantageously with the use of aqueous or corresponding alcoholic bases, such as those described above, or lower alkanoic alkali metal lower alkoxides, e.g. ethanolic sodium ethoxide.

The compounds of the invention so obtained can be converted into each other according to known methods. For example, resulting compounds in which $R_2$, $R_3$ and/or $R_4$ stand for hydrogen, may be reacted with a reactive ester of the corresponding alcohol, e.g. that of a lower alkanol, for example, derived from a hydrohalic or sulfonic acid, to yield the corresponding mono-, di- or tri-lower alkyl compounds. Resulting unsaturated compounds, e.g. lower alkenyl, alkynyl or furfuryl compounds, can be hydrogenated as shown above, to yield the corresponding saturated, e.g. lower alkyl or tetrahydrofurfuryl compounds. Resulting lower alkyl esters may also be hydrolyzed or transesterified, for example, with the use of the above alkaline hydrolyzing or alcoholizing agents.

The compounds of the invention are obtained in the free form or in the form of their salts, depending on the conditions under which the process is carried out, the salts are also included in the present invention. These are particularly derived from the free acids and therapeutically useful inorganic or organic bases, primarily the alkali metal, alkaline earth metal, e.g. sodium, potassium, magnesium or calcium salts, or ammonium salts derived from ammonia or amines, such as those corresponding to the amino group $R_1$—N—$R_2$, e.g. mono-, di- or tri-lower alkylamines, -cycloalkylamines, -cycloalkyl-lower alkylamines or -aralkylamines, mixed amines or tertiary nitrogen bases, such as pyridine, collidine or lutidine. Said compounds of Formula I also form acid addition salts, preferably with therapeutically useful acids, such as mineral acids, e.g. hydrochloric, hydrobromic, sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4-aminosalicylic, embonic, nicotinic, methanesulfonic, ethanesulfonic, hydroxyethanesulfonic, ethylenesulfonic, halogen-benzenesulfonic, toluenesulfonic, napthalenesulfonic or sulfanilic acid; methionine, tryptophane, lysine or arginine.

The invention further includes any variant of the present process in which an intermediate product obtainable at any stage of the process is used as starting material and any remaining steps are carried out, or the process is discontinued at any stage thereof, or in which the starting materials are formed under the reaction conditions, for example, amides of Formula IV from nitriles, or in which the reaction components are used in the form of their salts. Mainly those starting materials should be used in the reactions of the invention that lead to the formation of those compounds indicated above as being especially valuable.

The starting material is obtained according to known methods, preferably those, illustrated by the examples herein. For example, the compounds of Formula III are obtained by condensing reactive esters of the alcohols $R_1$—OH, e.g. those mentioned above, or corresponding aldehydes, with compounds of the formula

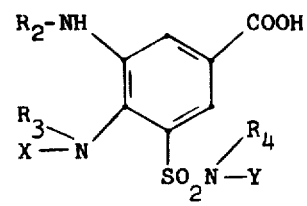

(obtainable according to the methods disclosed in J. Med. Chem., 1971, Vol. 14, No. 5, page 432) and hydrogenating any Schiff's base obtained, e.g. as shown above, or with the use of complex light metal hydrides, such as alkali metal borohydrides, e.g. sodium borohydride. Compounds of Formulae III and IV can also be prepared by condensing amines of the formula $R_3$—N-H—X or $R_3$—NH—Ph—$NH_2$ and

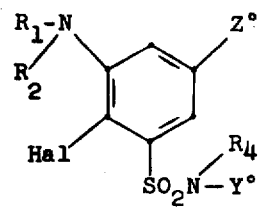

respectively, wherein Hal is a halogen atom, such as fluorine, chlorine, bromine or iodine, Z° is a free or correspondingly esterified or amidated carboxy group or cyano and Y° is either Y or $R_5$, preferably at elevated temperature and/or pressure. Representative members of said halogenated acids, or lower alkyl esters thereof, are described in J. Med. Chem., 1970, Vol. 13, No. 6, page 1071, showing also various methods according to which the above intermediates can be prepared. The corresponding amides or hydrazides are obtainable from said esters by amino- or hydrazinolysis, which process may take place simultaneously in the above condensation, when using compounds in which Z° is lower carbalkoxy.

Resulting mixtures of isomers, e.g. of compounds of Formulae I to III, can be separated into the single isomers by methods in themselves known, e.g. by fractional distillation, crystallization and/or chromatography. Racemic products can likewise be resolved into the optical antipodes, for example by separation of diastereomeric salts thereof, e.g. by the fractional crystallization of d- or l-tartrates or d-α-(phenyl or l-naphthyl)ethylamine or l-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or advantageously elevated temperatures, at atmospheric or superatmospheric pressure.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances, e.g. antihypertensives and/or psychotherapeutics, as illustrated by U.S. Pat. Nos. 3,288,678, 3,379,612, 3,499,082 and 3,515,786. Said pharmaceutical compositions are prepared according to conventional mixing, granulating or coating methods respectively and contain about 0.1 to 75%, preferably about 1 to 50% of the active ingredient.

The following examples illustrating the invention are not to be construed as being limitations thereon. Temperatures are given in degrees Centigrade and all parts wherever given are parts by weight.

EXAMPLE 1

The mixture of 2 g of 4-(4-acetamidophenylamino)-3-n-butylamino-5-sulfamoylbenzoic acid and 50 ml of 2N aqueous sodium hydroxide is refluxed for one hour under nitrogen. It is cooled, filtered and the filtrate acidified with glacial acetic acid to a pH of 4–5. The mixture is cooled in an ice bath, the precipitate formed filtered off and recrystallized from 50% aqueous ethanol, to yield the 4-(4-aminophenylamino)-3-n-butylamino-5-sulfamoylbenzoic acid of the formula

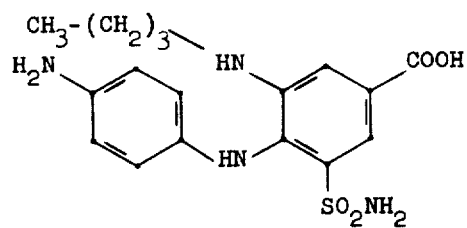

melting at 210° with decomposition.

The starting material is prepared as follows: The mixture of 5.6 g of 4-chloro-3-nitro-5-sulfamoylbenzoic acid, 200 ml of water and 9 g of 4-aminoacetanilide is refluxed for four hours while stirring under nitrogen. It is cooled to room temperature and the precipitate formed filtered off, to yield the 4-(4-acetamidophenylamino)-3-nitro-5-sulfamoylbenzoic acid, melting above 275°.

The mixture of 9.9 g thereof, 100 ml of water, 1 g of sodium hydroxide and 2.5 g of 10% palladium on charcoal is hydrogenated at room temperature and 2.8 atm until the theoretical amount of hydrogen has been absorbed. It is filtered, the filtrate acidified with concentrated hydrochloric acid, the precipitate formed filtered off, washed with water and recrystallized from aqueous ethanol, to yield the 4-(4-acetamidophenylamino)-3-amino-5-sulfamoylbenzoic acid melting at 280° with decomposition.

The mixture of 6.4 g thereof, 120 ml of methanol and 1.4 g of n-butyraldehyde is refluxed for one hour while stirring under nitrogen. It is cooled in an ice bath and 1.2 g of sodium borohydride are added to the solution while stirring under nitrogen. After stirring overnight at room temperature, the mixture is evaporated and the residue taken up in 50 ml of water. The solution is acidified with glacial acetic acid to a pH of 4–5, the precipitate formed filtered off and dissolved in 60 ml of 2N aqueous sodium hydroxide. The solution is washed with ethyl acetate, filtered, the filtrate acidified with concentrated hydrochloric acid and the precipitate formed filtered off, to yield the 4-(4-acetamidophenylamino)-3-n-butylamino-5-sulfamoylbenzoic acid.

EXAMPLE 2

The mixture of 3.9 g of 4-(4-acetamidophenylamino)-3-benzylamino-5-sulfamoylbenzoic acid and 39 ml of 2N aqueous sodium hydroxide is refluxed for 1 hour under nitrogen. After cooling to room temperature it is filtered and the filtrate acidified with glacial acetic acid to pH = 4. The precipitate formed is filtered off and recrystallized from aqueous ethanol, to yield the 4-(4-aminophenylamino)-3-benzylamino-5-sulfamoylbenzoic acid melting at 244° with decomposition.

The starting material is prepared as follows: To the mixture of 3.6 g of 4-(4-acetamidophenylamino)-3-amino-5-sulfamoylbenzoic acid, 20 ml of water and the sufficient amount of N aqueous sodium hydroxide to reach a pH = 7.4, 1.3 g of benzyl chloride are added while stirring at 30°. The mixture is stirred for 16 hours at room temperature, during which time 4N aqueous sodium hydroxide is added dropwise to keep said pH value. It is filtered, the filtrate acidified with 2 ml of glacial acetic acid and the precipitate formed filtered off, to yield the 4-(4-acetamidophenylamino)-3-benzylamino-5-sulfamoylbenzoic acid which is used as such without further purification.

EXAMPLE 3

The mixture of 0.9 g of 4-(4-acetamidophenylamino)-3-furfurylamino-5-sulfamoylbenzoic acid and 9 ml of 2N aqueous sodium hydroxide is refluxed for one hour under nitrogen, cooled, filtered and the filtrate acidified with glacial acetic acid to pH=4–5. The precipitate formed is filtered off, washed with water and recrystallized from 50% aqueous ethanol, to yield the 4-(4-aminophenylamino)-3-furfurylamino-5-sulfamoylbenzoic acid melting at 232° with decomposition.

The starting material is prepared as follows: The mixture of 6.6 g of 4-(4-acetamidophenylamino)-3-amino-5-sulfamoylbenzoic acid, 120 ml of methanol and 1.8 g of furfural is refluxed for one hour while stirring under nitrogen. It is cooled with ice, and 1.2 g of sodium borohydride are added portionwise while stirring and cooling. After stirring at room temperature overnight the mixture is evaporated under reduced pressure, the residue taken up in 50 ml of water, the solution acidified with glacial acetic acid to pH = 4.5, the precipitate formed filtered off and washed with water. It is taken up in 60 ml of 2N sodium hydroxide, the solution washed with ethyl acetate, filtered and the filtrate acidified with hydrochloric acid. The precipitate formed is filtered off, washed with water and recrystallized from 50% aqueous ethanol, to yield the 4-(4-acetamidophenylamino-3-furfurylamino-5-sulfamoylbenzoic acid melting at 250° with decomposition.

EXAMPLE 4

The mixture of 1 g of (4-acetamidophenylamino)-3-but-2-enylamino-5-sulfamoylbenzoic acid and 10 ml of 2N aqueous sodium hydroxide is refluxed for 1 hour under nitrogen. It is cooled, filtered, the pH of the filtrate adjusted to 4 with glacial acetic acid and the precipitate formed filtered off. It is washed with water and recrystallized from aqueous ethanol, to yield the 4-(4-aminophenylamino)-3-but-2-enylamino-5-sulfamoylbenzoic acid of the formula

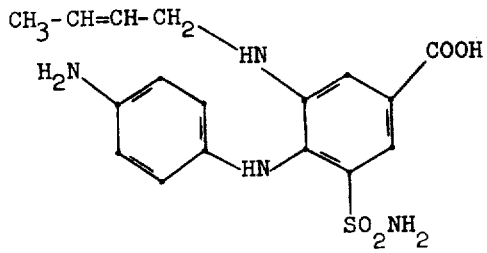

melting at 208° with decomposition.

The starting material is prepared as follows: To the stirred mixture of 5.5 g of 4-(4-acetamidophenylamino)-3-amino-5-sulfamoylbenzoic acid, 2.0 g of 1-bromo-2-butene, 30 ml of water and 10 ml of N aqueous sodium hydroxide, 4N aqueous sodium hydroxide is added dropwise in order to keep the pH of the mixture at 7.4 for 17 hours. It is filtered, the filtrate acidified with glacial acetic acid to pH = 4 and the precipitate formed filtered off. It is recrystallized from aqueous ethanol, to yield the 4-(4-acetamidophenylamino)-3-but-2-enylamino-5-sulfamoylbenzoic acid melting at about 230° with decomposition.

EXAMPLE 5

The mixture of 5.1 g of 4-(4-acetamidophenylamino)-3-(2-norborn-5-enylmethyl)-5-acetylsulfamoylbenzoic acid and 50 ml of 2N aqueous sodium hydroxide is refluxed for 2 hours under nitrogen. It is cooled, filtered, the filtrate acidified with glacial acetic acid to a pH of 4–5 and the precipitate formed filtered off. It is washed with water, dissolved in 40 ml of hot ethanol, the solution filtered and the filtrate diluted with water. After standing the precipitate formed is filtered off and again recrystallized from aqueous ethanol, to yield the 4-(4-aminophenylamino)-3-(2-norborn-5-enylmethyl)-5-sulfamoylbenzoic acid of the formula

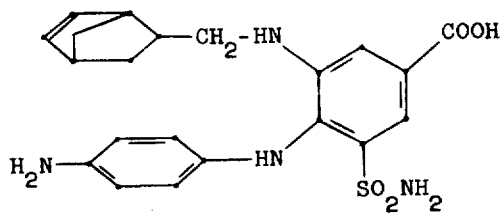

melting at 245° with decomposition.

The starting material is prepared as follows: The mixture of 20 g of 4-(4-acetamidophenylamino)-3-nitro-5-sulfamoylbenzoic acid and 200 ml of acetic anhydride is refluxed for ten minutes while stirring under nitrogen. It is evaporated under reduced pressure, the residue triturated with water and dissolved in 200 ml of 2N aqueous sodium hydroxide. The solution is washed with diethyl ether, filtered and acidified with concentrated hydrochloric acid to pH of 1–and the precipitate filtered off, to yield the 4-(4-acetamidophenylamino)-3-nitro-5-acetylsulfamoylbenzoic acid melting at 175°–185°.

The solution of 19.5 g thereof in 225 ml of water and 3.4 g of sodium hydroxide is hydrogenated over 5 g of 10% palladium on charcoal. After the theoretical amount of hydrogen has been absorbed, the mixture is filtered, the residue washed with water, the filtrate acidified with concentrated hydrochloric acid and cooled with ice. The precipitate formed is filtered off, washed with water and recrystallized from aqueous ethanol to yield the 4-(4-acetamidophenylamino)-3-amino-5-acetylsulfamoylbenzoic acid melting above 280°.

The mixture of 5 g thereof, 3 g of 2-norborn-5-enecarboxaldehyde and 50 ml of diethylene glycol dimethyl ether is stirred at 105°–110° for 5 hours under nitrogen. It is evaporated under reduced pressure at about 100° and the residue taken up in 100 ml of ethanol. The solution is cooled with ice and 5 g of sodium borohydride are added during 5 minutes while stirring and cooling. After stirring for 16 hours at room temperature the mixture is evaporated under reduced pressure and the residue taken up in 25 ml of water. The mixture is acidified with concentrated hydrochloric acid, diluted with 50 ml of water and heated to the boil. The precipitate formed after cooling is filtered off and recrystallized from 50% aqueous ethanol to yield the 4-(4-acetamidophenylamino)-3-(2-norborn-5-enylmethyl)-5-acetylsulfamoylbenzoic acid melting at 270° with decomposition.

EXAMPLE 6

The mixture of 2 g of 4-(4-acetamidophenylamino)-3-benzylamino-5-(2-acetamidophenylsulfamoyl)-benzoic acid and 20 ml of 2 N aqueous sodium hydroxide is refluxed for 6 hours under nitrogen. After cooling to room temperature it is filtered, the filtrate acidified with glacial acetic acid to a pH of 4–5 and the precipitate formed filtered off. It is washed with water, taken up in 50 ml of 50S hot aqueous ethanol, the precipitate formed after cooling is filtered off and again recrystallized from 25 ml of 50% aqueous ethanol, to yield the 4-(4-aminophenylamino)-3-benzylamino-5-(2-aminophenylsulfamoyl)-benzoic acid of the formula

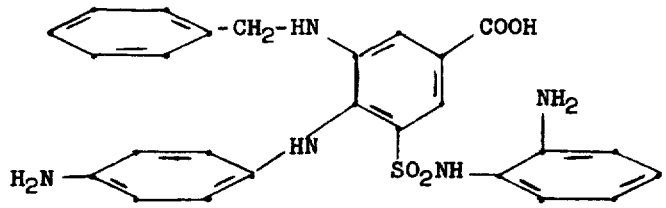

melting at 225° with decomposition.

The starting material is prepared as follows: The mixture of 38.8 g 4-chloro-5-chlorosulfonyl-3-nitrobenzoic acid, 39.9 g of 2-aminoacetanilide and 150 ml of dimethylformamide is stirred for 2½ hours at room temperature. It is poured into 1.7 lt of water and 20 ml of concentrated hydrochloric acid while stirring, the precipitate formed is filtered off and washed with water. It is dissolved in 600 ml of hot ethanol, 900 ml of hot water are added, the mixture filtered and the filtrate left in the cold, to yield the 4-chloro-5-(2-acetamidophenylsulfamoyl)-3-nitrobenzoic acid melting at 225°–227° with decomposition. [In the analogous manner the 5-(4-acetamidophenylsulfamoyl)-isomer is prepared, m.p. 245°–246° (dec.).]

The mixture of 8.3 g thereof, 9 g of 4-aminoacetanilide and 200 ml of water is refluxed for 4 hours while stirring under nitrogen. It is cooled to room temperature, acidified with concentrated hydrochloric acid to a pH of 1–2, the precipitate collected and recrystallized from 100 ml of 50% aqueous ethanol, to yield the 4-(4-acetamidophenylamino)-5-(2-acetamidophenylsulfamoyl)-3-nitrobenzoic acid, melting at 276° with decomposition. [In the analogous manner the 5-(4-acetamidophenylsulfamoyl)-isomer is prepared, m.p. 307° (dec.)].

The mixture of 12.1 g thereof, 150 ml of water, 23 ml of 2 N sodium hydroxide and 2.3 g of 10% palladium on charcoal is hydrogenated at room temperature until the theoretical amount of hydrogen has been adsorbed. It is filtered, the filtrate acidified with concentrated hydrochloric acid, the precipitate formed filtered off, washed with water and recrystallized from 110 ml of 50% aqueous ethanol, to yield the 4-(4-acetamidophenylamino)-3-amino-5-(2-acetamidophenylsulfamoyl)-benzoic acid melting at 252°–253°. [Similarly the 5-(4-acetamidophenylsulfamoyl)-isomer is prepared, m.p. 238°–239°.]

The mixture of 3 g thereof, 60 ml of diethyleneglycol dimethyl ether and 30 ml of benzaldehyde is heated to 105° for 4 hours and evaporated under reduced pressure. The residue is taken up in 100 ml of anhydrous ethanol, the solution cooled with an ice bath and 4.5 g of sodium borohydride are added portionwise while stirring. After 1 hour the ice bath is removed and the mixture stirred overnight at room temperature. Thereupon another 2.25 g of sodium borohydride are added, stirring is continued for 90 minutes and 150 ml of water are added. The mixture is filtered, the filtrate concentrated, the concentrate strongly acidified with hydrochloric acid, the precipitate collected and recrystallized from 50 ml of aqueous ethanol, to yield the 4-(4-acetamidophenylamino)-3-benzylamino-5-(2-acetamidophenylsulfamoyl)-benzoic acid melting at 268° with decomposition. [Analogously the 5-(4-acetamidophenylsulfamoyl)-isomer is prepared, m.p. 282° (dec.).]

EXAMPLE 7

The mixture of 1 g of 4-(4-acetamidophenylamino)-3-benzylamino-5-(4-acetamidophenylsulfamoyl)-benzoic acid and 10 ml of 2 N aqueous sodium hydroxide is refluxed for 1 hour under nitrogen. After cooling it is filtered, the filtrate acidified with glacial acetic acid to a pH of 4–5, the precipitate collected and recrystallized from 30 ml of 50% aqueous ethanol, to yield the 4-(4-aminophenylamino)-3-benzylamino-5-(4-aminophenylsulfamoyl)-benzoic acid melting at 238° with decomposition.

EXAMPLE 8

The mixture of 1.2 g of 4-(4-aminophenylamino)-3-furfurylamino-5-sulfamoylbenzoic acid (Example 3), 0.6 g of 10% palladium on charcoal and 120 ml of dioxane is hydrogenated at room temperature and atmospheric pressure until the theoretical amount of hydrogen has been absorbed (about 2 hours). It is filtered, the filtrate evaporated under reduced pressure, the residue is triturated with water, dissolved in 40 ml of 50% hot aqueous ethanol, the solution filtered hot, the filtrate cooled and the precipitate formed filtered off, to yield the 4-(4-aminophenylamino)-3-(2-tetrahydrofurylmethylamino)-5-sulfamoylbenzoic acid, melting at 253° with decomposition.

EXAMPLE 9

The mixture of 1.8 g of 4-(4-acetamidophenylamino-3-furfurylamino-5-(2-acetamidophenylsulfamoyl)-benzoic acid and 18 ml of 2 N aqueous sodium hydroxide is refluxed for 6 hours under nitrogen. After cooling to room temperature it is acidified with glacial acetic acid to a pH of 4-5, the precipitate collected and recrystallized from 6 ml of 50% aqueous ethanol, to yield the 4-(4-aminophenylamino)-3-furfurylamino-5-(2-aminophenylsulfamoyl)-benzoic acid melting at 182° with decomposition.

Similarly the 4-(4-aminophenylamino)-3-furfurylamino-5-(4-aminophenylsulfamoyl)-benzoic acid is prepared, m.p. 193° (dec.).

The starting material is prepared as follows: The mixture of 4-(4-acetamidophenylamino)-3-amino-5-(2-acetamidophenylsulfamoyl)-benzoic acid, 60 ml of diethyleneglycol diethyl ether and 30 ml of furfural is heated to 110° for 4 hours and evaporated under reduced pressure. The residue is taken up in 100 ml of anhydrous ethanol, the solution cooled with an ice bath and 4.5 g of sodium borohydride are added portionwise while stiring. After one hour the ice bath is removed and the mixture stirred overnight at room temperature. Thereupon 2.25 g of sodium borohydride are added, the mixture stirred for 90 minutes and diluted with 150 ml of water. It is filtered, the filtrate concentrated and the concentrate strongly acidified with hydrochloric acid. The precipitate formed is collected and recrystallized twice from 50% aqueous ethanol, to yield the 4-(4-acetamidophenylamino)-3-furfurylamino-5-(2-acetamidophenylsulfamoyl)-benzoic acid melting at 258° with decomposition. [Analogously the 5-(4-acetamidophenylsulfamoyl)-isomer is prepared m.p. 266° (dec.)].

EXAMPLE 10

The mixture of 1.3 g of 4-(4-acetamidophenylamino)-3-but-2-enylamino-5-(4-acetamidophenylsulfamoyl)-benzoic acid and 13 ml of 2 N aqueous sodium hydroxide is refluxed for 1 hour under nitrogen. After cooling to room temperature it is filtered, the filtrate acidified with glacial acetic acid to a pH of 4-5 and the precipitate formed filtered off and washed with water, to yield the 4-(4-aminophenylamino-3-but-2-enylamino-5-(4-aminophenylsulfamoyl)-benzoic acid melting at about 130°.

The starting material is prepared as follows: To the solution of 2.5 g of 4-(4-acetamidophenylamino)-3-amino-5-(4-acetamidophenylsulfamoyl)-benzoic acid in 60 ml of water and 5 ml of N potassium hydroxide, 0.7 g of 1-bromo-2-butene are added dropwise while stirring. The pH of the mixture is kept at 7.4 by subsequent addition of 4 N aqueous potassium hydroxide. After about 15 minutes the mixture is filtered, the filtrate acidified with glacial acetic acid to pH = 4, the precipitate formed filtered off and recrystallized from 50% aqueous ethanol, to yield the 4-(4-acetamidophenylamino)-3-but-2-enylamino-5-(4-acetamidophenylsulfamoyl)-benzoic acid melting at 265° with decomposition.

EXAMPLE 11

Preparation of 10,000 tablets each containing 5 mg of the active ingredient:

| Formula: | |
|---|---|
| 4-(4-aminophenylamino)-3-furfurylamino-5-sulfamoyl-benzoic acid | 50.0 g |
| Lactose | 1,207.0 g |
| Corn starch | 75.0 g |
| Polyethylene glycol 6.000 | 75.0 g |
| Talcum powder | 75.0 g |
| Magnesium stearate | 18.0 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

Similarly, 5 mg tablets are prepared from the remaining compounds of the invention, e.g. those illustrated by the previous examples.

I claim:
1. A compound corresponding to the formula

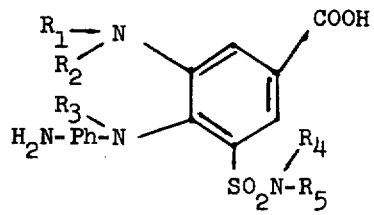

in which $R_1$ is lower alkyl, lower alkenyl, lower alkynyl, (monocyclic, 3 to 7 ring-membered cycloalkyl, cycloalkenyl, 2- or 7-norbornanyl or 2-norborn-5-enyl)-$C_mH_{2m}$, Ph is 1,2-, 1,3- or 1,4-phenylene, unsubstituted or substituted by one member of lower alkyl, hydroxy, lower alkoxy, halogeno or trifluoromethyl, $m$ is an integer from 0 to 4, $R_2$ is hydrogen, lower alkyl, lower alkenyl or lower alkynyl, each of $R_3$ and $R_4$ is hydrogen or lower alkyl, and $R_5$ is hydrogen, lower alkyl or Ph-$NH_2$, or the therapeutically useful ammonium, alkali or alkaline earth metal or acid addition salts thereof.

2. A compound as claimed in claim 1 and corresponding to the formula

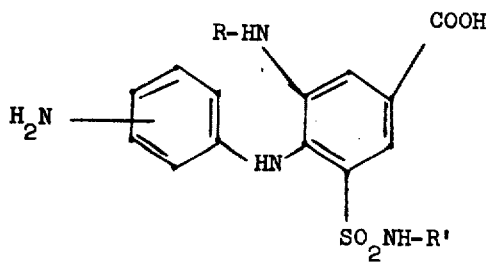

wherein R is alkyl or alkenyl with 3 to 7 carbon atoms, (3 to 7 ring-membered cycloalkyl, 2- or 7-norbornanyl or 2-norborn-5-enyl -methyl or -ethyl, R' is hydrogen or aminophenyl, or therapeutically useful ammonium, alkali metal or acid addition salts thereof.

3. A compound as claimed in claim 2, in which formula R is alkyl or 2-alkenyl with 4 or 5 carbon atoms, cyclopropylmethyl, 2-norborn-5-enylmethyl, and R' is hydrogen, or therapeutically useful ammonium, alkali metal or acid addition salts thereof.

4. A compound as claimed in claim 2 and being the 4-(4-aminophenylamino)-3-n-butylamino-5-sulfamoyl-benzoic acid or a therapeutically useful alkali metal, ammonium or acid addition salt thereof.

* * * * *